(12) United States Patent
Becker

(10) Patent No.: US 7,194,180 B2
(45) Date of Patent: *Mar. 20, 2007

(54) FIBER DETECTOR APPARATUS AND RELATED METHODS

(75) Inventor: Richard Becker, Anaheim, CA (US)

(73) Assignee: Biolase Technology, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/417,762

(22) Filed: May 3, 2006

(65) Prior Publication Data

US 2006/0210228 A1 Sep. 21, 2006

Related U.S. Application Data

(63) Continuation of application No. 10/964,799, filed on Oct. 13, 2004, now Pat. No. 7,068,912, which is a continuation of application No. 10/029,586, filed on Oct. 24, 2001, now Pat. No. 6,829,427.

(60) Provisional application No. 60/242,936, filed on Oct. 24, 2000.

(51) Int. Cl.
G02B 6/00 (2006.01)
G02B 6/36 (2006.01)

(52) U.S. Cl. .................. 385/134; 385/77; 385/147; 250/227.28

(58) Field of Classification Search .................. 385/77, 385/78, 85, 139, 147, 134; 356/73.1; 250/227.14, 250/227.28
See application file for complete search history.

(56) References Cited

U.S. PATENT DOCUMENTS 5,061,033 A * 10/1991 Richard ................ 385/92
5,349,137 A * 9/1994 Cedrone ................ 174/76
5,353,147 A * 10/1994 Grimes .................. 398/28
5,452,391 A * 9/1995 Chou et al. ............ 385/92
5,625,733 A * 4/1997 Frigo et al. ............ 385/88
5,898,807 A * 4/1999 Welsh .................... 385/56
6,325,551 B1* 12/2001 Williamson III et al. ..... 385/88
6,533,466 B1* 3/2003 Smith .................... 385/75
6,829,427 B1* 12/2004 Becker ................... 385/147

FOREIGN PATENT DOCUMENTS

DE 3303624 C1 * 7/1984
EP 753906 A2 * 1/1997
JP 08254634 A * 10/1996

* cited by examiner

*Primary Examiner*—John D. Lee
(74) *Attorney, Agent, or Firm*—Stout, Uxa, Buyan & Mullins, LLP

(57) ABSTRACT

A fiber detector apparatus includes a hub having one or more electrical contacts. The hub is configured to be placed against a connector, which is disposed on an electromagnetic energy source, such that electrical continuity is established between the electrical contacts of the hub and electrical contacts on a connector plate of the electromagnetic energy source. The number and positions of the electrical contacts correlate with the presence and characteristics of one or more fibers extending through the hub toward the electromagnetic energy source. A data storage microcircuit may also be provided within the hub to store identification information about the fibers being used. Knowing the physical characteristics of the fibers being used in a particular procedure can permit a user of the apparatus to improve the effectiveness of a procedure using the electromagnetic energy.

22 Claims, 3 Drawing Sheets

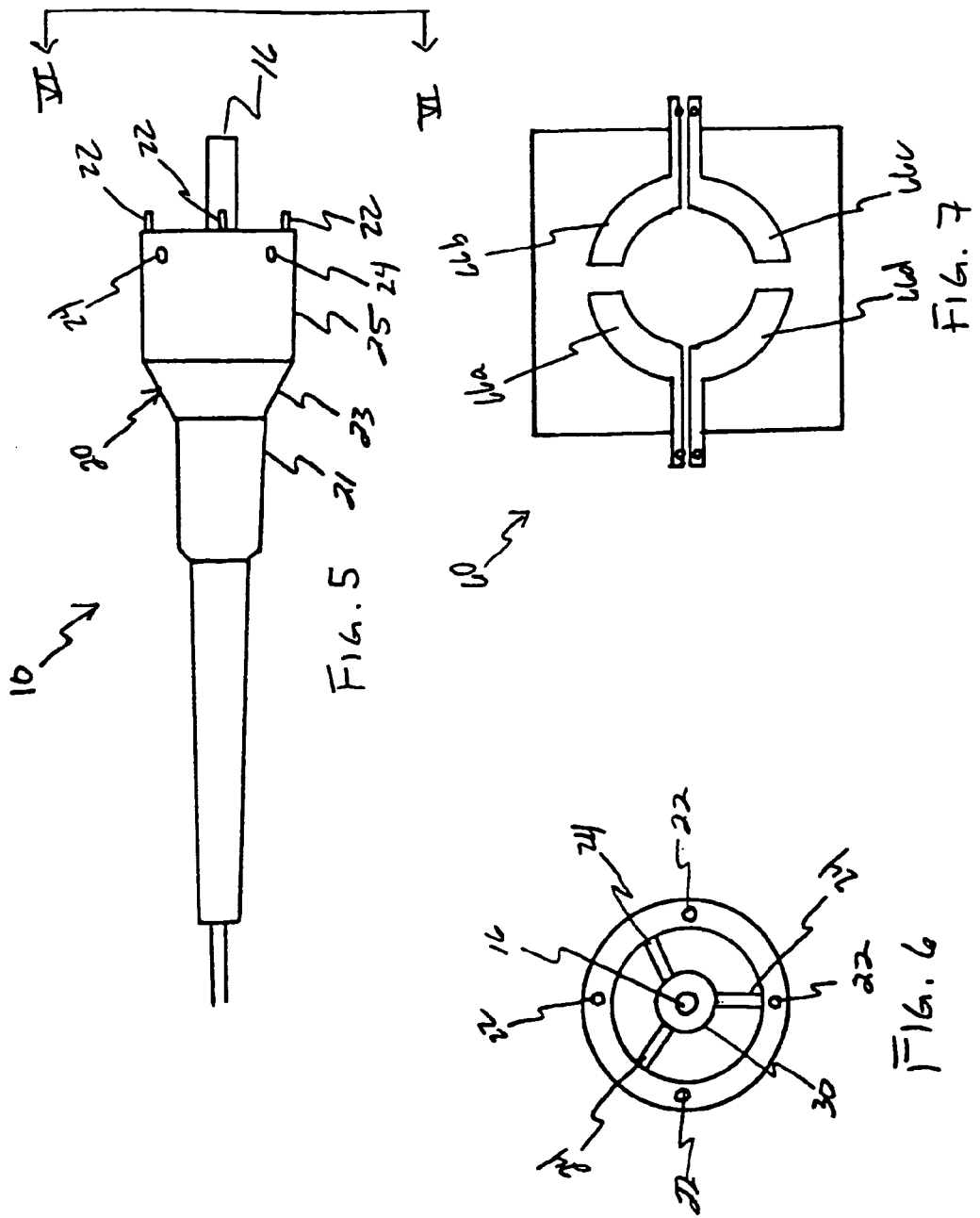

FIBER DETECTOR APPARATUS AND RELATED METHODS

CROSS-REFERENCE TO RELATED APPLICATIONS

This application is a continuation of U.S. application Ser. No. 10/964,799, filed Oct. 13, 2004, now U.S. Pat. No. 7,068,912, which is a continuation of U.S. application Ser. No. 10/029,586, filed Oct. 24, 2001, now U.S. Pat. No. 6,829,427, which claims the benefit of U.S. Provisional Application No. 60/242,936, filed Oct. 24, 2000, the entire contents of all which are hereby incorporated by reference.

BACKGROUND OF THE INVENTION

Optical cutters are well-known in medical, dental, and industrial settings. Generally, optical cutters employ a source of electromagnetic energy, such as a laser source, and an optical fiber system connected to the laser source and configured to direct the laser through one or more optical fibers to a surface to be cut. The optical fiber system may include one or more optical fibers contained within an optical fiber tube. The optical fiber tube may have a device at its end (the distal end) for controlling the delivery of the laser to the surface to be cut. The other end (the proximal end) of the optical fiber tube is connected to the laser source.

The fiber tubes may contain one or more optical fibers that may differ in certain physical properties. The laser's effectiveness is influenced by the physical properties of the optical fibers, such as length, diameter, shape, and/or type of fiber (e.g., material). Thus, it is important to know the physical properties of the optical fibers so that one using an optical cutter can improve the performance, reliability, and effectiveness of the device depending on which optical fiber is being used at any particular time.

Accordingly, there remains an unmet need for a device that permits detection of a fiber, and permits identification of the properties of the fiber.

SUMMARY OF THE INVENTION

The present invention fulfills this need and provides an apparatus and methods for detecting fibers, such as optical fibers. In particular, the invention provides an apparatus and methods for determining characteristics of fibers, such as length, shape, diameter, and type of the fibers.

The apparatus of the invention includes a hub with one or more electrical contacts that are able to transmit information, such as identification information, about the fibers being used with the apparatus so that the information can be used to improve the effectiveness of material removal using electromagnetic energy, such as a laser. The apparatus of the invention provides information, such as fiber length, fiber diameter, fiber shape, numerical aperture, and fiber material, which can be used to provide an accurate description of the conditions of use of the laser energy, and specific parameters, such as power delivered, energy density, incision size, and cutting time, related to the procedure. This information allows the user to adjust his or her technique to be highly effective in treating patients, processing industrial material, or in controlling/programming the electromagnetic energy device and any fluid delivery parameters.

In one embodiment of the invention, a fiber detector apparatus comprises a hub having a proximal end and a distal end, and having a longitudinal axis through a lumen extending through the proximal and distal ends, wherein the hub is structured to receive a fiber guide tube through the lumen. The hub comprises a plurality of electrical contacts that provide fiber identification information of a fiber within the fiber guide tube, and the electrical contacts are provided at a leading surface of the proximal end of the hub. The electrical contacts may be in electrical communication with each of the other electrical contacts. In one embodiment, the electrical contacts are pins, and may be retractable.

In another embodiment of the invention, a fiber guide assembly comprises a fiber guide tube having both a fiber guide extending therethrough and a hub positioned around the fiber guide tube at an end of the fiber guide tube, wherein the hub includes a plurality of pins at the proximal end of the hub. The assembly of the invention may comprise one or more fibers, such as optical fibers, extending through the fiber guide tube. The pins of the assembly may be retractable into the hub of the assembly. The number and position of the pins of the assembly may be indicative of characteristics of the fibers in the fiber guide tube. The assembly may include a material remover at the distal end of the fiber guide tube, which may be used for removal of biological or industrial materials.

In another embodiment of the invention, the hub used in the apparatus and/or assembly of the invention may include a microcircuit for storing data about the fibers. The microcircuit is preferably in electrical contact with the pins of the hub.

In yet another embodiment of the invention, a method of detecting a fiber attached to a hub comprises the steps of: (a) providing a hub having a plurality of pins at a proximal end of the hub; (b) placing a circuit board into electrical contact with the pins, wherein the number and position of the pins contacting the circuit board determine a coding sequence indicative of the presence of a fiber; and (c) decoding the coding sequence to determine whether the fiber is attached to the hub.

In practicing the foregoing method, the hub may have at least three pins for determining the characteristics of the fiber, including the fiber's length, shape, diameter, and type. In addition, or alternatively, the hub may include a microcircuit for storing data about the fiber. The foregoing method may also comprise a step of determining the fiber tip's power density.

Any feature or combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description and claims.

BRIEF DESCRIPTION OF THE DRAWINGS

FIG. 5 is a side elevation view of a fiber detector apparatus of the invention with four electrical contacts.

FIG. 6 is a front elevation view of the fiber detector apparatus of FIG. 5 along line VI—VI.

FIG. 7 is a front elevation view of a contact plate for use with the fiber detector apparatus of FIG. 5.

DETAILED DESCRIPTION OF THE PRESENTLY PREFERRED EMBODIMENTS

Although the disclosure herein refers to the use of a fiber detector apparatus that is used to detect and provide information about optical fibers used with a laser source that is used to remove material from surfaces, such as biological surfaces, the apparatus of the invention is not to be limited to such uses. The apparatus may be used to detect fibers in any system where the physical properties of the fibers are important determinants in the operation of the system. In addition, any other source of energy may be transmitted through the fibers, and the devices may be used to remove material from any type of surface amenable to such procedures. For example, in addition to medical applications, the apparatus may be used in devices that are used to etch material from relatively hard surfaces like silicon chips. In addition, the apparatus of the invention may be used in optical systems that employ optical fibers for directing light energy to a surface to be examined.

Figure 1:
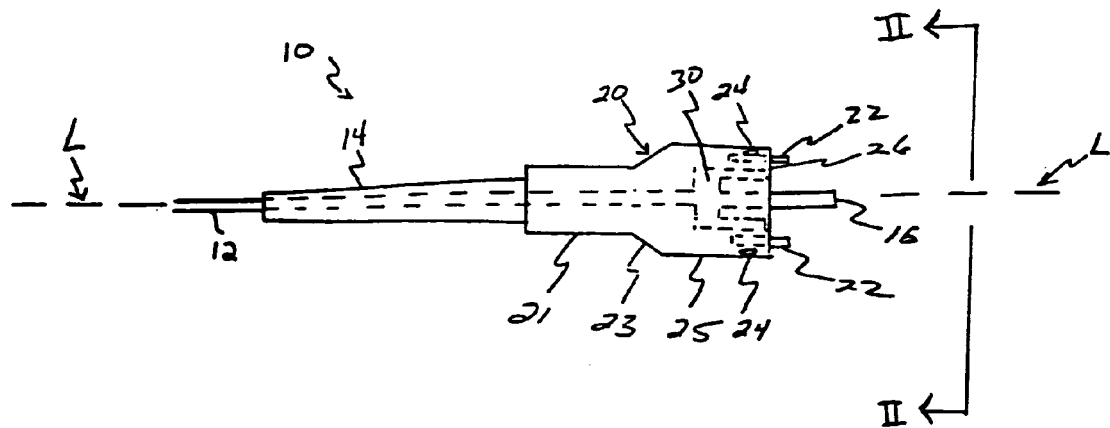
FIG. 1 is a side elevation view of a fiber detector apparatus of the invention.

Referring to the figures, and specifically FIG. 1, a fiber detector apparatus 10 is illustrated. Fiber detector apparatus 10 includes a hub 20 positioned at one end of fiber guide tube 12. The apparatus of the invention is a coupling between an electromagnetic source, such as a laser source, and a fiber that can transmit the electromagnetic energy from the electromagnetic source, such as an optical fiber. The apparatus may find particular use as a coupler between a material remover that uses a laser to facilitate removal of material and an optical fiber. The apparatus of the invention is provided at one end of a tube. At the other end of the tube, the material remover may be attached. In a presently preferred embodiment, the material remover comprises the fiber guide tube 12 and an atomizer controlled by a laser source. In an alternative embodiment, the material remover merely comprises an output end (e.g., fiber tip) of the fiber guide tube 12 and, in accordance with one definition, including the laser source that provides the energy. Examples of preferred types of material removers, the accompanying laser sources (e.g., delivery systems) and related equipment, and their methods of use are disclosed in U.S. Pat. Nos. 6,288,499; 6,231,567; 6,086,367; 5,785,521; and 5,762,501; the entire contents of which are incorporated herein by reference.

In reference to the disclosure herein, the tube 12 extending through the apparatus of the invention is referred to as a fiber guide tube, and the tube includes a proximal end disposed near the laser source, and a distal end disposed away from the laser source. In other words, the proximal end refers to the end of the tube or assembly that is close to the laser source when the assembly is connected to the laser source, and the distal end is the other end of the assembly (e.g., the end used to remove material). Thus, when referring to the proximal end of the apparatus described herein, reference is being made to the end of the apparatus that will contact the laser source.

Hub 20 is illustrated as a generally cylindrical structure comprising three longitudinal portions, namely, distal cylindrical portion 21, sloped cylindrical portion 23, and proximal cylindrical portion 25. Hub 20 is configured as a housing for fiber guide tube 12. Although hub 20 is illustrated with three longitudinal portions, hub 20 may also be configured with more or fewer portions; for example, hub can be a single cylinder. In addition, although hub 20 is illustrated with a generally cylindrical cross section, other cross-sectional shapes may be employed, such as rectangular shapes. Hub 20 is manufactured from any suitable rigid material capable of structurally retaining the components of the apparatus of the invention, described herein. Examples of suitable materials include plastics, metals, and specifically, metal alloys. The hub can be made by any conventional method known to those skilled in the art. For example, the hub can be manufactured by cast molding.

Fiber guide tube 12 is attached to fiber connector 30 at one end of the tube. Fiber connector 30 connects fiber guide tube 12 to fiber guide 16, which extends from fiber connector 30, and is preferably formed as an integral unit of fiber connector 30. Alternatively, fiber guide 16 is not integrally formed with fiber connector 30. Fiber guide tube 12 is a tubular structure that houses one or more fibers, such as optical fibers. Fiber guide tube may also be understood to be a tube that encompasses a single fiber, in which case the fiber guide tube may be considered to be the cladding of the single fiber. In addition, the fiber guide tube may house one or more tubes for transmitting additional substances to a material remover, such as a tubing for air, or tubing(s) for one or more liquids, such as water. In embodiments wherein the fiber guide tube houses a plurality of optical fibers, or other tubes for additional substances, fiber guide tube 12 may be made of any suitable material that is strong yet flexible, for example, plastic, such as polyethylene tubing.

Figure 2:
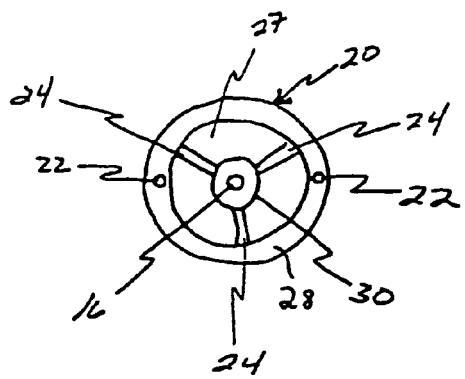
FIG. 2 is a front elevation view of the fiber detector apparatus of FIG. 1 along line II—II.

Fiber connector 30 is secured within lumen 27 of hub 20 by the clamping actions imposed on connector 30 by screws 24, as illustrated in FIG. 2. Screws 24 are designed to compress against connector 30, and wedge the connector so that it is substantially limited in movement with respect to hub 20. In one embodiment of the invention, three screws are provided approximately 120 degrees apart along a rotational angle about the longitudinal axis L illustrated in FIG. 1. Thus, the three screws act to hold connector 30 within hub 20 by each forcing the connector towards the other screws. As a result of the connector 30 being connected to fiber guide tube 12, the fiber guide tube 12 is also connected to hub 20.

Although screws are used in one embodiment of the invention, other methods of clamping connector 30 to hub 20 may be employed as will be appreciated by those skilled in the art.

As shown in FIGS. 1 and 2, hub 20 has a proximal leading surface 26, which is in abutting relationship to a connector of a laser source when the apparatus of the invention is connected to the source, as described herein. As illustrated in FIG. 1, hub 20 includes a plurality of pins 22 extending from and beyond proximal leading surface 26. Pins 22 are electrical contacts that establish electrical continuity between a conductive terminal on the laser source. Thus, pins 22 should be made of any conductive material, such as a metal (e.g., copper or gold) or a conductive or resistive rubber or semi-insulative and/or insulatives material. In an embodiment wherein the pins are formed of a resistive, semi-insulative, insulative and/or other material, the circuit of the laser device can be configured to detect such materials. In the illustrated embodiment, pins 22 are configured such that they are in electrical contact with each other within hub 20. As illustrated in FIG. 1, two pins are provided; however, any number of pins may be provided depending on the information to be transmitted through the pins, as described herein. In preferred embodiments, the hub includes between one and ten pins. The pins may be retractable and thus be urged into hub 20 when they are pressed against a surface. Accordingly, when pins 22 are in contact with conductive leads on the laser source, they are preferably urged into hub 20. When pins are not in contact with a surface, they preferably extend from proximal surface 26. Although pins are illustrated in FIG. 1, any electrical contact may be utilized on proximal leading surface 26, such that the electrical contact will be in physical contact with conductive terminals on the laser source, and that electrical signals can be transmitted therebetween.

In an additional embodiment of the invention, pins 22 may be provided within a lumen 27 formed by a circumscribing wall 28 of hub 20 to provide some protection to the pins from physical damage. As will be understood by persons skilled in the art, the mating surface on the electromagnetic source would have to be configured to permit the electrical contact between the pins of the hub and the conductive terminals of the electromagnetic source.

The arrangement and number of pins 22 (or electrical contacts) provided on hub 20 determine a coding sequence. A specific coding sequence is provided for a specific type of fiber. The correlation between a coding sequence and a particular fiber is predetermined prior to the manufacture of the device of the invention. The coding sequence may be sensed by a printed circuit board, or any insulated plate with metal on it that acts similarly to a circuit board. In reference to the disclosure herein, the printed circuit board is located on the energy source, such as the laser device. The strips of metal on the circuit board are contacted by the pins and are electrically connected together, resulting in a set of connections. The metal contacts on the circuit board are preferably raised (e.g., see FIG. 4) from the base of the circuit board. In one embodiment, as a result of the metal contacts being raised, the contacts will urge pins 22 of hub 20 into the body of the hub when the pins are in contact with the metal contacts of the circuit board. When a pin does not contact a metal contact, the pin is not urged into the body of the hub. Thus, the particular set and configuration of connections including whether the pin is extending from, or retracted into, the hub, work together to determine the coding sequence. These connections may be decoded by any conventional electrical means, as will be readily appreciated by those skilled in the art, and thereby result in the identification of the coding sequence and the determination of the fiber guide tube characteristics. For example, computer instructions that are provided in the laser source, either as software or hardware instructions, may be used to read the electrical signals produced by the apparatus of the invention when it is connected to the laser source. As a further example, the set of values encoded by the position and number of pins can be stored in a lookup table that may then be searched by the program(s) in the laser device to determine whether a fiber is present, and to determine the physical properties of the fiber. In one embodiment of the invention, the metal contacts on the contact plate can be arranged in concentric circles thereby for example avoiding the specific alignment of the hub and the plate.

One example of a set of coding sequences is listed in Table I below. This particular example is based on four pins provided on hub 20. As will be evident, up to seven different code combinations may be obtained in this example. The number of different code combinations in the illustrated embodiment is determined by the equation: number of code combinations=$(2^n)-1$, where "n" is the number of pins minus one. In that regard, one pin may act as a return, an aligning device, or both, and the three other pins may or may not be inserted into the hub when contacting the circuit board.

TABLE I

| | Position | | | |
|---|---|---|---|---|
| | 1 | 2 | 3 | 4 |
| Code 1 | Pin | X | Pin | X |
| Code 2 | Pin | Pin | X | X |
| Code 3 | Pin | X | X | Pin |
| Code 4 | Pin | Pin | Pin | X |
| Code 5 | Pin | X | Pin | Pin |
| Code 6 | Pin | Pin | X | Pin |
| Code 7 | Pin | Pin | Pin | Pin |

In another embodiment, the number of different code combinations is determined by the equation: number of code combinations=$2^n$, where "n" is the number of pins minus one. In this embodiment, a Code 8 would have the code combination of Pin, X, X, X. In yet another embodiment, the number of different code combinations is determined by the equation: number of code combinations=$2^n$, where "n" is the number of pins. In this embodiment, Pin 1 is not used as a return and can take on either of the values "Pin" or "X." The apparatus of the invention may also include a protective member 14 positioned at the distal end of hub 20. Protective member 14 is configured to provide some physical protection to fiber guide tube 12, for example, by preventing excessive bending or kinking in tube 12. Protective member 14 can be made of any suitable material, for example, rubber, and is preferably configured integral with or to be inserted into the distal end of hub 20.

The fiber detector assembly of the invention can be made by inserting a fiber guide tube through the protective member and hub, and connecting the fiber guide tube to the fiber connector. In another embodiment, the fiber guide tube is first secured to the fiber connector and, subsequently, inserted distally through the protective member and hub. The fiber connector can then be secured within the hub by tightening the screws of the hub to fixedly retain the fiber connector.

Figure 3:
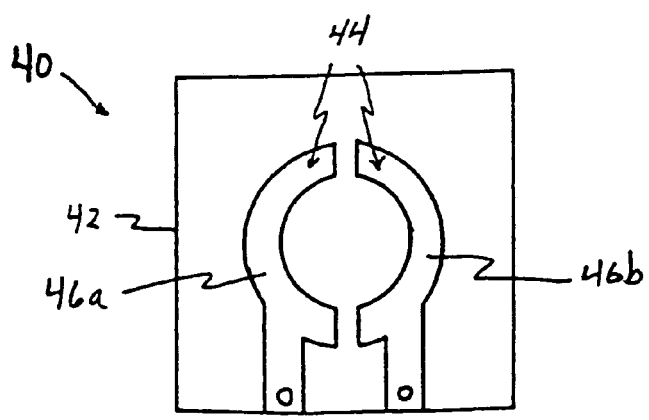
FIG. 3 is a front elevation view of a contact plate for use with the fiber detector apparatus of FIG. 1.

FIG. 3 illustrates an example of a printed circuit board 40 configured to be used with the apparatus of the invention. Circuit board 40 generally consists of an insulated, or non-conductive, base 42 having conductive regions 44 thereon. Any type of conductive material may be used as understood by those skilled in the art. As illustrated, conductive regions 44 are illustrated as metallic traces. The illustrated circuit board 40 of FIG. 3 is configured to be used with a fiber detector apparatus having two pins as described, supra. Thus, circuit board 40 includes two metallic traces 46a and 46b. The fiber detector apparatus is positioned on the laser source so that the pins of the apparatus contact each of the metallic traces 46a and 46b.

Figure 4:
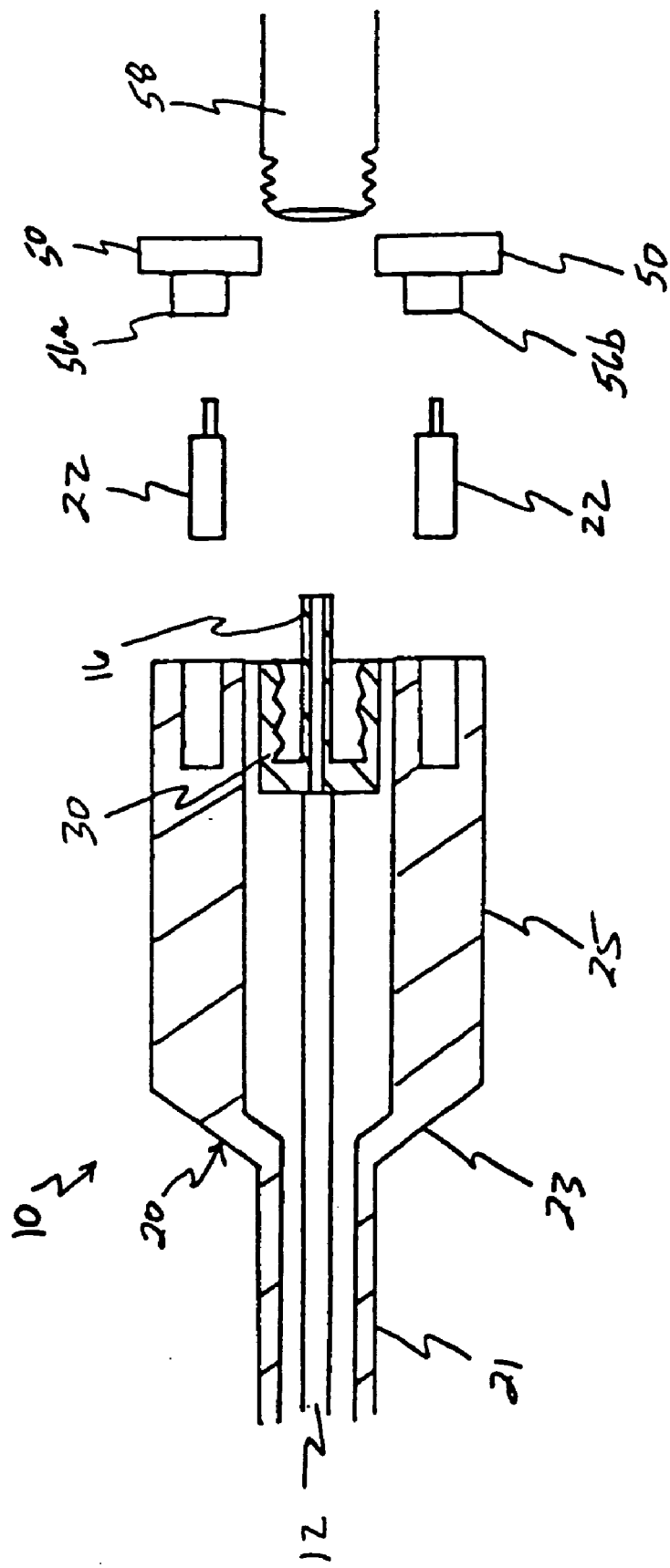
FIG. 4 is a partial, cross-sectional exploded view of a fiber detector apparatus and a contact plate to contact the fiber detector apparatus.

FIG. 4 illustrates a cross-sectional, exploded view of a fiber detector apparatus of the invention and a connector plate to receive the apparatus. Connector plate 50, which may be used with or in place of the circuit board 40, is illustrated with two metallic traces 56a and 56b to contact pins 22 of the fiber detector apparatus when the apparatus is connected to the connector plate 50. As illustrated, connector plate 50 should be configured to permit the transmission of energy from the internal fiber connector assembly 58 to fiber guide 16, which permits transmission of the energy to the fiber or fibers in the fiber guide tube 12. The connector plate 50 illustrated in FIG. 4 includes a centrally located hole to permit the insertion of fiber guide 16 into fiber connector assembly 58. Although connector plate 50 is shown and described with respect to an electromagnetic energy source, the connector plate can be used on any suitable object, including personal computer boards.

FIG. 5 illustrates a fiber detector apparatus 10 that has four pins 22. As illustrated, each of the four pins are spaced approximately ninety degrees apart about the longitudinal axis extending through the apparatus, as shown in FIG. 6. However, the exact position may vary, as described herein, in order to provide an indication of particular fiber characteristics used with the apparatus of the invention.

FIG. 7 illustrates a front elevation view of a connector plate 60, which similar to the connector plate 50 of FIG. 4 but configured to be used with a fiber detector apparatus having four pins as illustrated in FIG. 5. Connector plate 60 is illustrated with four metallic traces 66a, 66b, 66c, and 66d to contact the pins of the fiber detector apparatus. In addition, connector plate 60 includes a centrally located hole to permit insertion of the fiber guide of the fiber detector apparatus.

The fiber detector apparatus of the invention may also include a microcircuit positioned within hub 20. One example of a suitable microcircuit is the publicly available Dallas DS2430A device (Dallas Semiconductor Corp. Dallas, Tex., USA). The Dallas DS2430A is a 256 bit, 2 wire electrically erasable programmable read only memory (EEPROM). The microcircuit may also be understood to be a hub data storage assembly. Other suitable devices will be readily recognized by those skilled in the art. Data about the fiber or fibers in the fiber guide tube may be stored in the microcircuit. Data that may be stored in such a microcircuit may include, but is not limited to, fiber guide diameter, fiber guide material, fiber guide numerical aperture, hours of use, date of manufacture, and serial number of the instrument. Data may be recorded at the time of manufacture, or the microcircuit may gather and store data while it is in use. For example, the microcircuit could have an identification code embedded in it, and/or store new data as required or configured. The data embedded in the device can be transferred to or from the microprocessor of the laser source and then be interpreted by software in the laser source. The instrument software may then make decisions based on the information stored in the microcircuit, and even store new data in the microcircuit. In such an embodiment, it is possible to use one or two pins in the hub, as compared to the four pin embodiment described supra.

As discussed herein, the apparatus of the invention may be used to detect whether a fiber is attached to the apparatus. Such a method may be practiced using a hub having two pins, which will electrically contact and connect two traces of a printed circuit board. The connection of the two traces may be used as a signal to the electromagnetic energy source through microprocessor software to notify it that a fiber is attached.

An apparatus having four pins is able to store a greater amount of information about the fiber(s) than an apparatus only having two pins. The identification information may include the size, shape, diameter, and type of fiber(s) attached to the apparatus. Such information may be used to determine the power density delivered at the tip of the fiber(s). Thus, software can gather the characteristics of the fiber(s), and use that information in conjunction with information pertaining to the laser source to determine the power density of the fiber(s). By determining the characteristics of the fiber(s), the method is also inherently determining whether a fiber is detected.

In one particular example, a clinician may use a laser with a fiber optic delivery system. The energy loss in the delivery system varies with fiber diameter, fiber aperture, and fiber material. These variables can be stored in a hub data storage assembly, such as a microcircuit, or encoded in pin position and number. When the hub is attached to the laser device, the microprocessor of the laser device may interrogate the stored data (either in the microcircuit, or in the number and position of the pins) and may recalculate the delivered energy. This new value of delivered energy may then be displayed to the user. In this way, the user can select an amount of delivered energy appropriate to the procedure being performed by for example adjusting the source of electromagnetic energy.

Alternatively, the user can select a desired energy level, and the laser device may adjust its output power to compensate for the losses mentioned, or other characteristics, resulting from the physical properties of the optical fibers. The fiber detector apparatus of the invention accordingly offers the ability for the instrument to provide feedback to the user, offering more information about power, energy, and power/density being delivered to the patient. Another advantage of the apparatus of the invention is that the user will conveniently and reliably be able to know characteristics of fiber diameter, and thus, will be able to determine for example the amount and distribution of fluid (e.g., air and/or water) to be used in conjunction with the laser energy. For example, specific sizes, distributions and combinations of atomized fluid particles may be determined as a result of the type of fiber being used. Another advantage of the apparatus of the invention is that the user will conveniently and reliably be able to know the fiber diameter, and thus, may more readily be able to determine or generate for example the proper incision size and/or cutting time for a particular procedure.

As another specific example, a clinician may insert the fiber detector apparatus into the connector of the laser device, and the software recognizes the code sequence conveyed by the retractable pins or the microcircuit, as described herein. As discussed herein, the code sequences may include data of fiber diameter, fiber length, fiber material, fiber shape, fiber tip configuration, fiber numerical apertures, and other relevant information. The code sequences may also be translated into the fiber diameter, and internal tables, which store for example the loss versus diameter information, and which can be used to correct or compare the displayed power to or with the calculated delivered power. A display (audio or visual) can advise the clinician of these parameters and the clinician can adjust his technique to take these parameters into consideration. By way of example, and not by way of limitation, if the numerical aperture is small, the user may want to keep the fiber tip further from the treatment site to decrease energy density.

Thus, as will be apparent from the foregoing disclosure, the apparatus of the invention which includes a hub having one or more pins, and possibly a microcircuit for storing data, can store identification information, such as physical properties, about the fibers used with the apparatus. This identification information can then be transmitted to a laser device where it can be decoded and analyzed. Additional information can then be displayed to the user of the device to permit the user to optimize the procedure being performed.

Examples of applications of the present invention can include medical, industrial, dental laser, telecommunications, and other sensor applications. In each of these applications, wherein the main device is desired to meet some accuracy or performance standard, and an external device is attached to the main device, the present invention can be incorporated. With such incorporation, the external device characteristics may be determined and allowed for, and the main device performance may be augmented. Medical instruments with measuring devices (e.g., transducers) with widely varying characteristics, and whose overall measurement accuracies may need to be high, can employ systems in accordance with the present invention. In such applications, the systems can interrogate the transducers and compensate for the transducer characteristics in order to guarantee or augment overall accuracy and performance.

While this invention has been described with respect to various specific examples and embodiments, it is to be understood that the invention is not limited thereto and that it can be variously practiced with the scope of the following claims.

What is claimed is:

1. A fiber identification apparatus, comprising:
   a member having a proximal end and a distal end, and having a longitudinal axis extending between the proximal and distal ends, wherein the member is structured to receive at least one fiber that is constructed to be coupled to a material remover;
   a plurality of movable couplers that provide information relating to the at least one fiber, the number and position of the movable couplers being indicative of one or more of a fiber length, fiber shape, fiber diameter, fiber configuration, fiber numerical aperture, fiber material and fiber type; and
   a microcircuit in communication with the movable couplers.

2. The apparatus of claim 1, wherein the at least one fiber is suitable for transmitting electromagnetic energy from an electromagnetic energy source.

3. The apparatus of claim 1, wherein the at least one fiber is an optical fiber.

4. The apparatus of claim 1, wherein the material remover comprises a source of electromagnetic energy and an atomizer.

5. The apparatus of claim 4, wherein the source of electromagnetic energy comprises a laser.

6. The apparatus of claim 1, wherein the number and position of the movable couplers is indicative of fiber length, fiber shape, fiber diameter, fiber configuration, fiber numerical aperture, fiber material and fiber type, to thereby provide a description of the conditions of use of the material remover.

7. The apparatus of claim 1, wherein:
   the material remover comprises an electromagnetic energy device and a fluid delivery; and
   the number and position of the movable couplers facilitate controlling or programming of the electromagnetic energy device and the fluid delivery.

8. The apparatus of claim 1, wherein the movable couplers are retractable pins.

9. A fiber guide assembly, comprising:
   at least one fiber having a proximal end and a distal end constructed to be coupled to a material remover,
   a plurality of movable couplers positioned in proximity to the proximal end of the fiber, the number and position of the plurality of movable couplers being indicative of one or more of a length, shape, diameter, configuration, numerical aperture, material and type of the at least one fiber, and
   a microcircuit in communication with the movable couplers.

10. The apparatus of claim 9, wherein the at least one fiber is suitable for transmitting electromagnetic energy from an electromagnetic energy source.

11. The apparatus of claim 9, wherein the at least one fiber is an optical fiber.

12. The apparatus of claim 9, wherein the material remover comprises a source of electromagnetic energy and an atomizer.

13. The apparatus of claim 12, wherein the source of electromagnetic energy comprises a laser.

14. The apparatus of claim 9, wherein the number and position of the movable couplers is indicative of fiber length, fiber shape, fiber diameter, fiber configuration, fiber numerical aperture, fiber material and fiber type, to thereby provide a description of the conditions of use of the material remover.

15. The apparatus of claim 9, wherein:
   the material remover comprises an electromagnetic energy device and a fluid delivery; and
   the number and position of the movable couplers facilitate controlling or programming of the electromagnetic energy device and the fluid delivery.

16. The apparatus of claim 9, wherein the movable couplers are retractable pins.

17. A method of detecting a fiber, comprising:
   (a) providing a plurality of movable couplers;
   (b) placing a circuit into communication with the movable couplers, wherein at least one property of the movable couplers is indicative of the presence of a fiber;
   (c) determining a presence of a fiber, based upon the at least one property; and
   (d) determining characteristics of the fiber including one or more of the fiber's length, shape, diameter, configuration, numerical aperture, material and type, based upon the at least one property.

18. The method of claim 17, wherein the movable couplers are retractable pins.

19. The method of claim 17, wherein the fiber is suitable for transmitting electromagnetic energy from an electromagnetic energy source.

20. The method of claim 19, wherein the electromagnetic energy source comprises an atomizer.

21. The method of claim 20, wherein the electromagnetic energy source comprises a laser and the fiber is an optical fiber.

22. The method of claim 17, wherein:
   the fiber is coupled to an electromagnetic energy device, which is disposed in proximity to a fluid delivery; and
   the number and position of the movable couplers facilitate controlling or programming of the electromagnetic energy device and the fluid delivery.

* * * * *